US00PP23243P2

(12) United States Plant Patent
Danziger

(10) Patent No.: US PP23,243 P2
(45) Date of Patent: Dec. 4, 2012

(54) ***PORTULACA* PLANT NAMED 'DPAZ15'**

(50) Latin Name: *Portulaca oleracea*
Varietal Denomination: DPAZ15

(75) Inventor: Gavriel Danziger, Moshav Mishmar Hashiva (IL)

(73) Assignee: Danziger 'DAN' Flower Farm (IL)

( * ) Notice: Subject to any disclaimer, the term of this patent is extended or adjusted under 35 U.S.C. 154(b) by 34 days.

(21) Appl. No.: 13/068,526

(22) Filed: May 13, 2011

(51) Int. Cl.
*A01H 5/00* (2006.01)

(52) U.S. Cl. ..... Plt./471

(58) Field of Classification Search ..... Plt./471
See application file for complete search history.

*Primary Examiner* — Susan McCormick Ewoldt
(74) *Attorney, Agent, or Firm* — Cassandra Bright

(57) ABSTRACT

A new and distinct *Portulaca* cultivar named 'DPAZ15' is disclosed, characterized by abundant flowering and an intense orange/red flower color. The new variety has a compact, semi trailing growth habit and forms a low, spreading plant. The new variety is a *Portulaca*, normally produced as an outdoor garden or container plant.

2 Drawing Sheets

Latin name of the genus and species: *Portulaca oleracea.*
Variety denomination: 'DPAZ15'.

BACKGROUND OF THE INVENTION

The new *Portulaca* cultivar is a product of a planned breeding program conducted by the inventor, Gavriel Danziger, in Moshav Mishmar Hashiva, Israel. The objective of the breeding program was to produce new *Portulaca* varieties for ornamental commercial applications. The cross resulting in this new variety was made during September 2008.

The seed parent is the unpatented, proprietary seedling variety referred to as *Portulaca oleracea* 'PT-8-441' The pollen parent is unknown, as the crossing resulting in 'DPAZ15' was an open pollination, with unidentifiable pollen parents. The new variety was discovered in June 2009 by the inventor in a group of seedlings resulting from the 2008 crossing, in a research greenhouse in Moshav Mishmar Hashiva, Israel.

Asexual reproduction of the new cultivar 'DPAZ15' by vegetative cuttings was first performed at a research greenhouse in Moshav Mishmar Hashiva, Israel in July 2009 and has shown that the unique features of this cultivar are stable and reproduced true to type in successive generations.

SUMMARY OF THE INVENTION

The cultivar 'DPAZ15' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DPAZ15' These characteristics in combination distinguish 'DPAZ15' as a new and distinct *Portulaca* cultivar:

1. Highly floriferous
2. Compact and dense semi trailing habit
3. Low spreading growth habit
4. Intense red/orange flower color.

Plants of the new cultivar 'DPAZ15' are similar to plants of the seed parent, *Portulaca oleracea* 'PT-8-441' in most horticultural characteristics, however, plants of the new cultivar 'DPAZ15' have a more compact plant habit, and more flowers per plant. Additionally, the new cultivar begins flowering earlier and produces more lateral branches than the seed parent.

COMMERCIAL COMPARISON

Plants of the new cultivar 'DPAZ15' are comparable to the commercial variety *Portulaca* 'BALRIORG' U.S. Plant Pat. No. 17,421. These *Portulaca* varieties are similar in most horticultural characteristics, including flower color and form. The new variety 'DPAZ15' differs in having more flowers, per plant, larger foliage and a more mounded, dense plant form than 'BALRIORG'. Additionally, the new variety has a more intense and homogenous flower color.

BRIEF DESCRIPTION OF THE PHOTOGRAPHS

Figure 1:
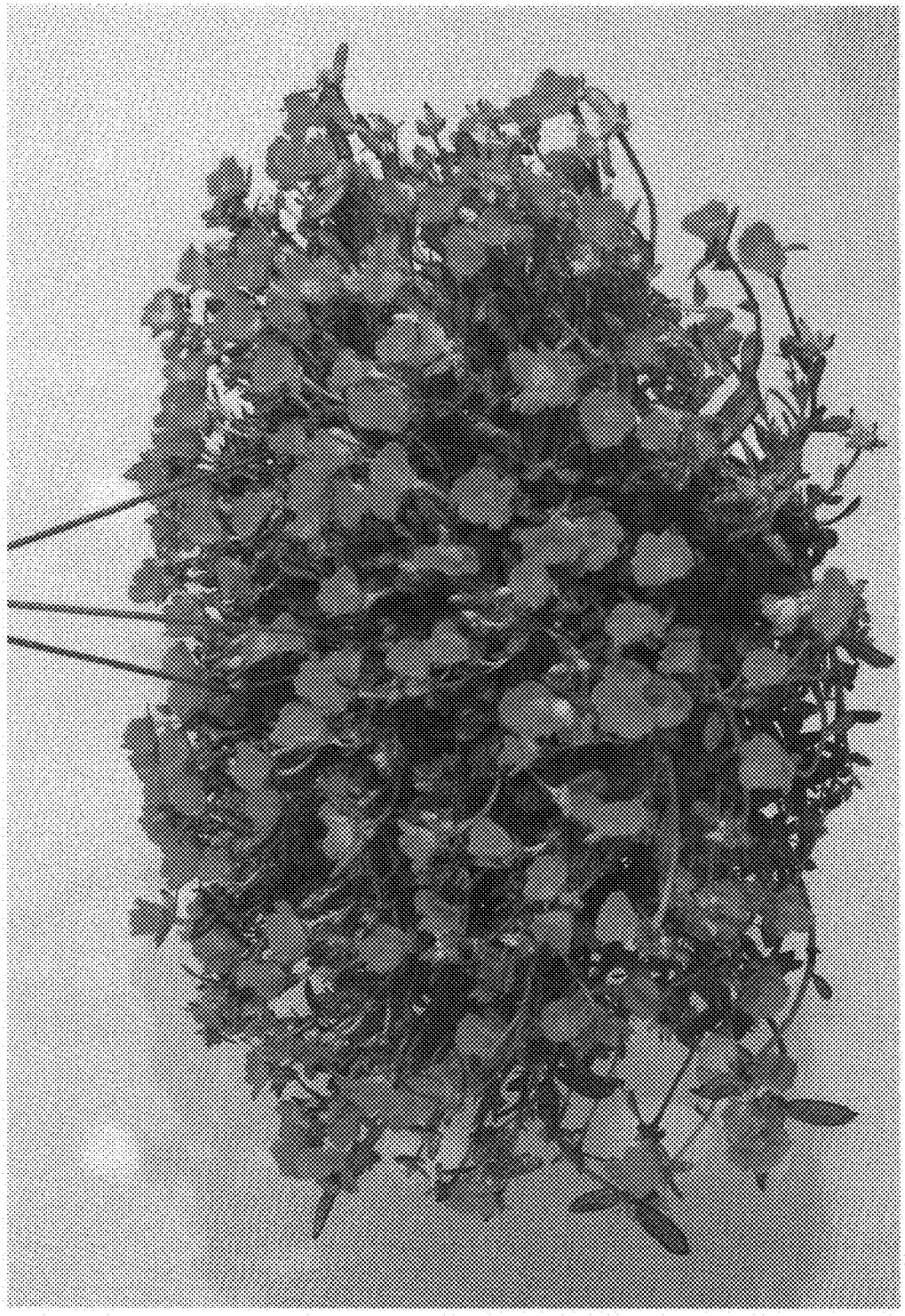

The accompanying photograph in FIG. 1 illustrates in full color a typical plant of 'DPAZ15' grown in a greenhouse, in a 13 cm basket. Age of the plant photographed is approximately 85 days from a rooted cutting.

Figure 2:
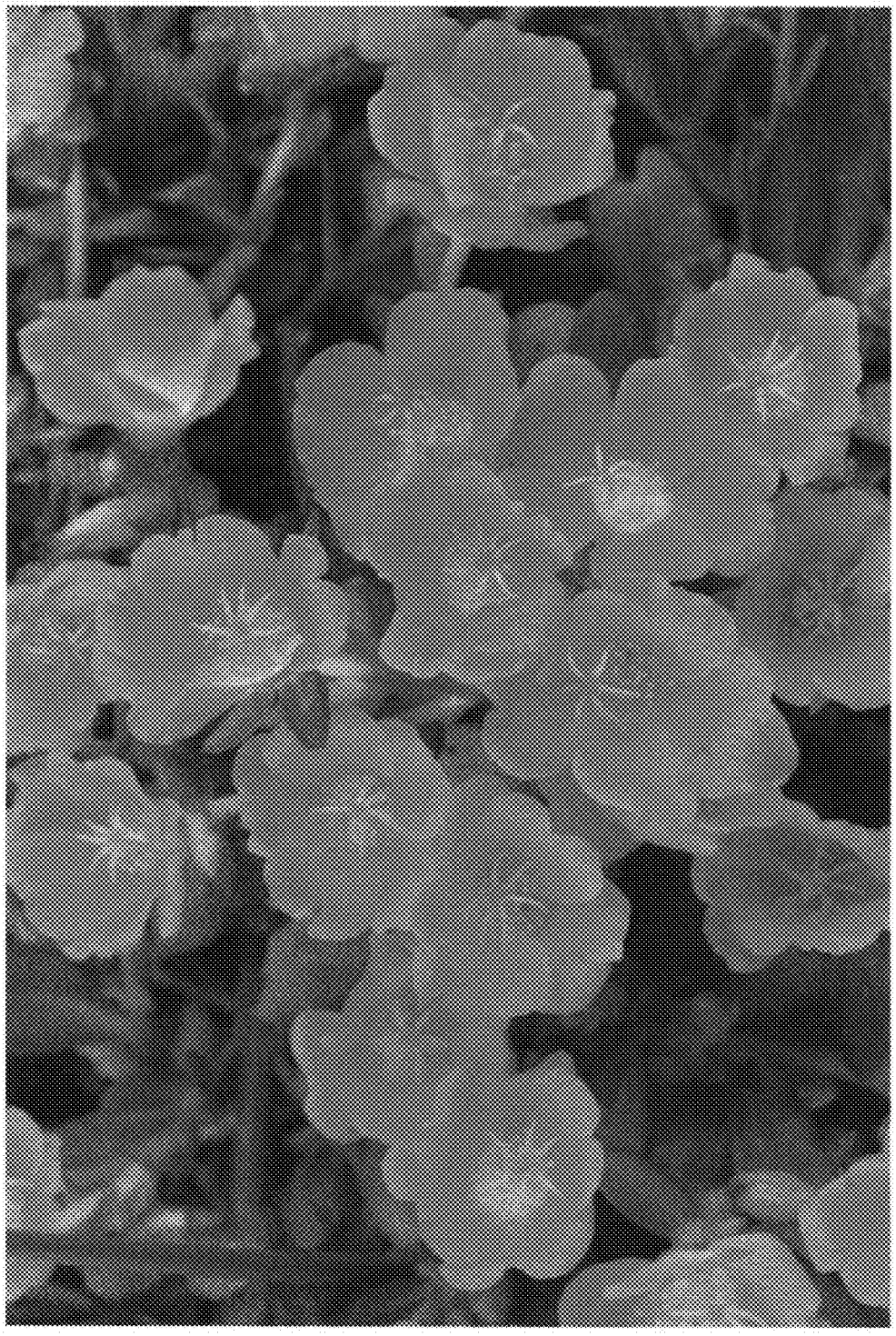

FIG. 2 illustrates in full color a close up of a typical bloom of 'DPAZ15'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001 except where general terms of ordinary dictionary significance are used. The following observations and measurements describe 'DPAZ15' plants grown in a greenhouse during Spring in Gilroy, Calif. The growing temperature ranged from 14° C. to 30° C. during the day and from 10° C. to 23° C. during the night. General light conditions are bright, normal sunlight. Measurements and numerical values represent averages of typical plant types.

Botanical classification: *Portulaca oleracea* 'DPAZ15'.

PROPAGATION

Time to initiate roots: 10 to 14 days at approximately 18-21° C.
Root description: Fibrous, spreading and dense.

PLANT

Growth habit: Mounded, semi-trailing.
Pot size of plant described: 13 cm.
Age of plant described: Approximately 80 days.
Height: 15 to 20 cm.
Plant spread: About 30 cm.
Growth rate: Medium vigor.
Branching characteristics: Tight, compact, dense branching.
Length of primary lateral branches: 30 cm.
Diameter of lateral branches: 0.3-0.5 cm.
Quantity of primary lateral branches: About 9.
Characteristics of primary lateral branches:
*Form*.—Horizontal. Rounded with ridges along the branch.
*Diameter*.—Approximately 0.4 cm.
*Color*.—From the base RHS Greyed-Orange 166A, at the tip RHS Yellow-Green 144B.
*Texture*.—Glabrous.
*Strength*.—Very strong.
Internode length: Approximately 3 cm.

FOLIAGE

Leaf:
*Arrangement*.—Alternate.
*Quantity*.—Approximately 14 per branch.
*Average length*.—About 3.3 cm.
*Average width*.—1.3 cm.
*Shape of blade*.—Most mature leaves are obovate, young leaves elliptic.
*Apex*.—Some are rounded and some acute.
*Base*.—Attenuate.
*Margin*.—Entire.
*Texture of top surface*.—Glabrous, smooth.
*Pubescence*.—None.
*Attachment*.—At right angle or obtuse angle to stem.
*Color*.—Young foliage upper side: RHS Green 137 B. Young foliage under side: RHS Green 137 B. Mature foliage upper side: RHS Green 137 C. Mature foliage under side: RHS Green 137 C.
*Venation*.—Type: Pinnate. Venation color upper side: RHS Green 137 C. Venation color under side: RHS Yellow-Green 147 C.
*Petiole*.—Length: 0.2 cm. Diameter: 0.2 cm. Color: Near RHS Green 143B. Texture: Glabrous.

FLOWER

Natural flowering season: From Spring to Autumn.
Days to flowering from rooted cutting: Approximately 8 weeks.
Inflorescence and flower type and habit: Terminal, single, sessile. Flower habit horizontal.
Rate of flower opening: 7 to 10 days from bud to fully opened flower.
Flower longevity on plant: Approximately 1 day.
Persistent or self-cleaning: Self-Cleaning.
Bud:
*Shape*.—Ovate with a pointed tip.
*Length*.—Approximately 0.8 cm.
*Diameter*.—Approximately 0.5 cm.
*Color*.—RHS Yellow-Green 144B with venation and top of RHS 144A.
Flower size:
*Diameter*.—Approximately 3.5 cm.
Corolla/petals:
*Arrangement*.—Single flower with five distinct overlapping petals.
*Length*.—Approximately 1.7 cm.
*Width*.—Approximately 1.4 cm.
*Quantity*.—5 petals.
*Texture*.—Glabrous.
*Apex*.—Emarginate.
*Shape*.—Obovate.
*Margin*.—Entire.
*Color*.—When opening: Upper surface: Near RHS Orange-Red 33A with center near Yellow 13A. Lower surface: Near RHS Orange 26B. Fully opened: Upper surface: RHS Orange-Red 32A. Lower surface: RHS Orange 24B.
Calyx/sepals:
*Quantity per flower*.—2.
*Shape*.—Deltoid.
*Length*.—Approximately 0.7 cm.
*Width*.—Approximately 0.5 cm.
*Apex*.—Acute.
*Base*.—Fused.
*Margin*.—Entire.
*Texture*.—Glabrous.
*Color*.—Upper and Lower Surface: Near RHS Yellow-Green 144C with venation and top of RHS Red-Purple 60B.
Peduncle: None.
Fragrance: None.

REPRODUCTIVE ORGANS

Stamens:
*Number*.—Approximately 70.
*Filament length*.—Approximately 0.5 cm.
Anthers:
*Shape*.—Oval, bi-lobed.
*Length*.—Approximately 0.5 mm.
*Color*.—Near RHS Yellow-Orange 21A.
*Pollen*.—Color: Near RHS Yellow-Orange 23A. Quantity: Moderate.
Pistil:
*Number*.—1 per flower.
*Length*.—0.75 cm.
*Style*.—Length: 0.5 cm. Color: Near RHS Yellow 2B.
*Stigma*.—Shape: Six-branched stigma. Color: Near RHS Orange 26A with darker color in the center — near RHS Orange-Red 32A. Ovary Color: Near RHS Yellow-Green 144C.

OTHER CHARACTERISTICS

Seeds and fruits: Fruits are egg-shaped 4-5 mm long with a conical shape top. Seeds are glossy black with a circular shape.
Disease/pest resistance: Neither resistance nor susceptibility to diseases or insects has been observed.
Temperature tolerance: Will not tolerate temperatures below 7° C.

What is claimed is:

1. A new and distinct cultivar of *Portulaca* plant named 'DPAZ15' as herein illustrated and described.

* * * * *